United States Patent
Ingman et al.

(10) Patent No.: US 9,925,218 B2
(45) Date of Patent: Mar. 27, 2018

(54) COMPOSITION, METHOD AND KIT FOR FORMATION OF GALVANIC CELLS ON THE SKIN

(71) Applicant: PILOGICS L.P., Haifa (IL)

(72) Inventors: Dov Ingman, Herzliya (IL); Erez Manor, Herzlia (IL)

(73) Assignee: PILOGICS L.P., Haifa (IL)

( * ) Notice: Subject to any disclaimer, the term of this patent is extended or adjusted under 35 U.S.C. 154(b) by 0 days.

(21) Appl. No.: 14/905,807

(22) PCT Filed: Jul. 17, 2014

(86) PCT No.: PCT/IB2014/063198
§ 371 (c)(1),
(2) Date: Jan. 17, 2016

(87) PCT Pub. No.: WO2015/008255
PCT Pub. Date: Jan. 22, 2015

(65) Prior Publication Data
US 2016/0151417 A1   Jun. 2, 2016

(30) Foreign Application Priority Data

Jul. 17, 2013 (IL) .................................. 227522

(51) Int. Cl.

| | | |
|---|---|---|
| *A61K 33/34* | (2006.01) | |
| *A61K 9/48* | (2006.01) | |
| *A61K 33/30* | (2006.01) | |
| *A61K 9/00* | (2006.01) | |
| *A61K 8/19* | (2006.01) | |
| *A61K 8/25* | (2006.01) | |
| *A61K 8/27* | (2006.01) | |
| *A61K 8/02* | (2006.01) | |
| *A61K 8/11* | (2006.01) | |
| *A61K 9/107* | (2006.01) | |
| *A61K 9/50* | (2006.01) | |
| *A61N 1/20* | (2006.01) | |
| *A61Q 7/02* | (2006.01) | |
| *A61Q 7/00* | (2006.01) | |

(52) U.S. Cl.
CPC ............ *A61K 33/34* (2013.01); *A61K 8/0241* (2013.01); *A61K 8/11* (2013.01); *A61K 8/19* (2013.01); *A61K 8/25* (2013.01); *A61K 8/27* (2013.01); *A61K 9/0009* (2013.01); *A61K 9/0014* (2013.01); *A61K 9/4816* (2013.01); *A61K 33/30* (2013.01); *A61N 1/205* (2013.01); *A61Q 7/00* (2013.01); *A61Q 7/02* (2013.01); *A61K 9/107* (2013.01); *A61K 9/501* (2013.01); *A61K 2800/412* (2013.01); *A61K 2800/413* (2013.01); *A61K 2800/83* (2013.01); *A61K 2800/88* (2013.01)

(58) Field of Classification Search
CPC ........ A61K 2800/412; A61K 2800/413; A61K 2800/83; A61K 2800/88; A61K 33/30; A61K 33/34; A61K 8/0241; A61K 8/11; A61K 8/19; A61K 8/25; A61K 8/27; A61K 9/0009; A61K 9/0014; A61K 9/107; A61K 9/48; A61Q 7/00; A61Q 7/02; A61N 1/205
See application file for complete search history.

(56) References Cited

U.S. PATENT DOCUMENTS

| | | | | |
|---|---|---|---|---|
| 5,262,149 | A * | 11/1993 | Sredni | A61K 31/14 424/600 |
| 7,194,316 | B2 * | 3/2007 | Bousfield | A61N 1/322 433/29 |
| 2006/0257437 | A1 * | 11/2006 | Ingman | A61K 8/19 424/401 |
| 2011/0118655 | A1 * | 5/2011 | Fassih | A61N 1/044 604/20 |

* cited by examiner

Primary Examiner — Aradhana Sasan
(74) Attorney, Agent, or Firm — Marc Van Dyke; Fourth Dimension IP

(57) ABSTRACT

Embodiments of the invention relate to a composition, method and kit for producing galvanic cells upon application of the composition to the skin. In some embodiments, the composition comprises encapsulated half-galvanic cell units (e.g. individual and/or autonomous half-galvanic cell units) having the same ox/red potential ($E°$), wherein each half-galvanic cell unit comprises metal particles in the range of nano- to micro size or a mixture thereof, suspended within an aqueous solution of soluble electrolytic salt of same metal and wherein each half-galvanic cell unit is encapsulated by internal layer(s) made of hydrophilic metal (including silicon) oxide nanoparticles and external layer(s) made of hydrophobic metal (including silicon) oxide nanoparticles. The composition is useful for preventing and/or treating alopecia or for enhancing hair growth.

11 Claims, No Drawings

COMPOSITION, METHOD AND KIT FOR FORMATION OF GALVANIC CELLS ON THE SKIN

FIELD OF THE INVENTION

The present invention relates to topically-applied compositions, for example, useful for promoting hair-growth.

BACKGROUND OF THE INVENTION

The following issued patents and patent publications provide potentially relevant background material, and are all incorporated by reference in their entirety: U.S. Pat. Nos. 5,514,167; 6,119,038; 6,443,915; 6,684,107; 7,133,725; 7,194,316; and 7,294,349.

SUMMARY OF EMBODIMENTS

Embodiments of the present invention relate to a new composition applicable for a wide scope of electrical dependent physiological applications, such as hair-care treatment, in particular for preventing alopecia and for renewing hair growth. In some embodiments, the composition comprises a non-polar medium (such as, liquid, semi-liquid, gel or paste-like) in which are spread separate, immiscible, multiple autonomous, stable entities, each comprising an encapsulated half-galvanic cell unit.

Each encapsulated half-galvanic cell comprises a metal in the form of colloidal particles immersed in an aqueous solution of its salt. Some embodiments relate to the use of the presently-disclosed composition for producing electrical current in situ within the treated skin in the baldness zone. It is speculated that such electrical current is formed by applying at least two presently-disclosed compositions, wherein each composition comprises encapsulated half-galvanic cell units of a particular ox/red potential which is different from the ox/red potential(s) of other composition(s). For example, one composition may comprise multiple encapsulated half-galvanic cell units, wherein each unit comprises metal A and aqueous solution of its salt which displays a particular E° and the other composition comprises multiple encapsulated half-galvanic cell units, wherein each half-galvanic cell unit comprises metal B and aqueous solution of its salt which displays a different E°. Actually, applying presently-disclosed compositions may lead to formation of multiple complete galvanic or battery cells within the treated baldness zone capable of generating electric current.

It seems that production of electric current in situ is a highly useful tool in treating baldness zones for hair growth. For example, it is speculated that applying to the baldness zone the presently-disclosed composition which comprises encapsulated half-galvanic cell units that contain Zn(s) and an electrolytic zinc salt, such as, for example, $ZnSO_4$(aq), $ZnCl_2$(aq) or $Zn(NO_3)_2$(aq) together with the presently-disclosed composition which comprises encapsulated half-galvanic cell units that contain Cu(s) and an electrolytic copper salt, such as, for example, $CuSO_4$(aq), $CuCl_2$(aq) or $Cu(NO_3)_2$(aq), resulted in production in situ of electric current within the treated baldness zone.

In addition, the presently-disclosed composition optionally comprises immiscible, autonomous, stable entities of hypotonic character relative to the treated skin, wherein each such entity comprises encapsulated water (or aqueous solution) droplets or may comprise a coated encapsulated water (or aqueous solution) droplets.

Embodiments of the invention provide a composition comprising individual autonomous entities, wherein each entity comprises encapsulated half-galvanic cell unit of same ox/red potential.

Some embodiments relate to the use of presently-disclosed compositions for producing in situ electric current within the skin in the baldness zone of a mammalian organism in a pico- to nano- amps range.

In some embodiments, an electric current for enhancing hair growth is produced in situ by applying to the treated skin of the baldness zone at least two presently disclosed composition wherein: (i) one composition comprises encapsulated half-galvanic cell units of a particular E° and (ii) the other composition comprises encapsulated half-galvanic cell units of different E°. It is speculated that upon applying the presently-disclosed compositions onto the skin of baldness zone which is an electrical conductivity environment, they form multiple complete galvanic cells that produce in situ electric current in a pico- to nano-amps range.

Some embodiments relate to a method for producing the aforementioned composition. The production method comprises encapsulated half-galvanic cell units, wherein each unit comprises an aqueous solution in which a metal, in a colloidal form, is present together with its soluble electrolytic salt.

Some embodiments relate to the use of any presently-disclosed composition for treating alopecia and for renewing hair growth.

It is now disclosed a composition comprising half-galvanic cell units (e.g. the half-galvanic cell units are individual and/or autonomous) (for example, the half-galvanic cell units have the same ox/red potential (E°)), wherein:

i. each half-galvanic cell unit comprises metal particles in the range of nano-to micro size or a mixture thereof; and/or ii. the half-galvanic cell units are suspended within an aqueous solution (e.g. of soluble electrolytic salt—for example, a salt of the same metal); and/or iii. each half-galvanic cell unit is encapsulated by internal layer(s) made of hydrophilic metal (including silicon) oxide nanoparticles and/or external layer(s) made of hydrophobic metal (including silicon) oxide nanoparticles.

In some embodiments, a size of each of the half-galvanic cell units is between at least 1 micron or at least 3 microns or at least 5 microns and/or at most 100 microns or at most 75 microns or at most 50 microns or at most 30 microns at most 25 microns.

Some embodiments relate to a kit for preventing alopecia and/or renewing hair growth and/or inducing hair-grow. The kit may comprise:

(i) at least two presently-disclosed or presently-claimed compositions wherein each composition comprises half-galvanic cell units of different E° value (e.g. the compositions may be maintained separately—i.e. not mixed with each other and not in fluid communication with each other—e.g. stored in different respective containers); and/or (ii) a net (e.g. elastic net) for facilitating ion movement—e.g. made of any combination of graphite, platinum or silver; and/or (iii) a container for mixing the at least two compositions.

DETAILED DESCRIPTION OF EMBODIMENTS

The invention is herein described, by way of example only.

For brevity, some explicit combinations of various features are not explicitly illustrated and/or described. It is now disclosed that any combination of the method or device features disclosed herein can be combined in any manner—including any combination of features—and any combination of features can be included in any embodiment and/or omitted from any embodiments.

Not wishing to be bound by theory, microcurrent is a physical therapy modality providing electric current in millionths of an ampere. This microcurrent stimulator has the ability to relieve pain, increase the rate of wound healing, increase protein synthesis, increase ATP synthesis, increase cell permeability, stimulate the regeneration of injured tissue, stimulate lymphatic flow and relieve myofascial trigger points. Because microcurrent flows at one millionth of an ampere it is delivered on the same scale as the current the body produces on its own in each cell, it is therefore of physiological value.

Microcurrent (typically less than 600 microamps) is a much smaller current than was previously available for clinical use. A smaller current—one that can penetrate the cell and balance the cell electrically—can restore a more normal physiological state to the damaged cells Small electrical charges may be helpful in initiating and perpetuating the numerous electrical chemical reactions in the healing process.

The physiological rationale behind the clinical effects of microcurrent therapy has not been ascertained. It would appear to be more clinically effective than other form of electrical stimulation for the following reasons:
- The microcurrent unit seems biologically more compatible.
- It is more effective in neutralizing the oscillating polarity of injured cells.
- The current below 600 microamps has a positive effect on increasing local availability of ATP.
- Microcurrent has probably a positive effect on increasing cell permeability.
- Microcurrent increases local protein synthesis.

A major drawback of all microcurrent treatments derived from the fact that a specific device should provide the microcurrent and the connection between such device and the treated patient is performed by means of contacting the human body to special electrodes.

Some embodiments of the present invention provide new approach to use an electric current for treating alopecia and for renewing hair growth in which a galvanic current, probably in a pico- to nano- amps range is formed in situ from chemical galvanic cells that are produced within the treated baldness zone from individual half-galvanic cell units.

More particularly, embodiments of the present invention provide a series of topical compositions of different E°, wherein each composition comprises individual autonomous half-galvanic cell units of same ox/red potential. Application of two or more compositions that are distinguished by displaying different E° values, namely the E° of half-galvanic cell units in one composition is different from the E° of half-galvanic cell units of other composition may produce an electric current by means of multiple complete galvanic cells that are formed within the skin in the baldness zone of a mammalian body.

In some embodiments, each of the encapsulated half-galvanic cell units comprises an aqueous suspension in which a particular metal, in a colloidal form, is present together with its soluble electrolytic salt. In such composition, all the half-galvanic cell units are of the same ox/red potential) (E°). A way of producing electric current in situ is considered possible by applying two or more presently-disclosed compositions, wherein each composition comprises encapsulated half-galvanic cell units of a different ox/red potential. When such half-galvanic cell units are in contact with the baldness zone, which is considered an electric conductivity environment, they are capable of producing multiple complete galvanic cells that provide a pico- to nano-amps range electric current. It is speculated that this generated electric current is effective in treating alopecia.

It was now unexpectedly and surprisingly found that such formation of encapsulated water droplets may be useful for producing autonomous half-galvanic cell units spread or suspended in a non-polar medium (such as, liquid, semi-liquid, gel or paste-like). More particularly, each of such individual encapsulated half-galvanic cell unit comprises a single metal in the form of nano- to micro colloidal particles (or a mixture thereof) immersed in an aqueous solution of its soluble electrolytic salt. For example, the encapsulated half-galvanic cell units of a first presently-disclosed composition may comprise $Zn(s)$ and its soluble electrolytic salt, such as $ZnSO_4(aq)$, $ZnCl_2(aq)$ or $Zn(NO_3)_2(aq)$, while the encapsulated half-galvanic cell units of the second presently-disclosed composition may comprise $Cu(s)$ and its soluble electrolytic salt, such as $CuSO_4(aq)$, $CuCl_2(aq)$ or $Cu(NO_3)_2(aq)$. When such two compositions which comprise encapsulated half-galvanic cell units of different ox/red potentials get together in contact with dermal layer(s) of the baldness zone, the encapsulated half-galvanic cell units are released into the surrounding electrical conductive medium which functions as a conductive salt (or ionic) bridge to allow the individual half-galvanic cell units to form multiple complete galvanic cell units, resulted in formation of multidirectional electric current in the pico- to nano-amps range.

As an optional salt (ionic) bridge, an elastic net made of graphite, silver or platinum, having protrusions for improving the contact with the skin in the baldness zone may be used for facilitating the ionic movement.

Thus, embodiments of relates to a composition which comprises autonomous, immiscible entities, comprising encapsulated half-galvanic cell units and optionally autonomous entities of hypotonic character relative to the skin of the treated baldness zone.

It further relates to apply such composition for treating and/or preventing alopecia and for renewing hair growth. Consequently, some embodiments relate to compositions which comprise autonomous encapsulated half-galvanic cell units for topical treatment of baldness regions and for affecting the activation of hair follicles. In addition, some embodiments relate to compositions that simultaneously comprise autonomous, encapsulated half-galvanic cell units and optionally autonomous encapsulated hypotonic entities, relatively to the scalp, wherein the encapsulated hypotonic entities play a role in the formation of flow of water from the hypotonic entities towards the skin and hypertonic half-galvanic cell units.

As a general scheme for depiction of such composition, one may visualize a medium comprises a non-polar liquid, such as oil, in which encapsulated half-galvanic cell units of same ox/red potentials) (E°) are spread. Each autonomous half-galvanic cell unit comprises a certain metal in the form of nano- to micro colloidal particles (or a mixture thereof) immersed in an aqueous solution of an electrolytic salt of same metal. Such composition may also contain encapsulated autonomous hypotonic entities relative to the skin in the treated baldness zone which comprises encapsulated water (or aqueous suspension) droplets. In addition, various hair-care ingredients are optionally dissolved in the non-polar medium.

Each individual half-galvanic cell unit is bounded or encapsulated by encapsulating material which comprises internal hydrophilic layer(s) and external hydrophobic layer(s) made of individual metal (including silicon) oxide nano-particles.

Definitions

For convenience, in the context of the description herein, various terms are presented here. To the extent that definitions are provided, explicitly or implicitly, here or elsewhere in this application, such definitions are understood to be consistent with the usage of the defined terms by those of skill in the pertinent art(s). Furthermore, such definitions are to be construed in the broadest possible sense consistent with such usage.

When 'particles' have diameter in the range of X and Y (where X and Y are both positive and have the dimension of length—e.g. microns or nanometers) this means that a mean diameter is in the range of X and Y. In some embodiments, this also means that at least 50% or at least 60% or at least 70% or a least 80% or at least 90% or at least 95% of the particles have an individual-particle diameter in the range of X and Y.

"Silicon" is included within the scope of the term "metal" when referred to as "metal-oxide." In contrast, 'metal particles' refer only to actual metals and not to silicon.

"Water" includes water or any aqueous suspension.

The term "nano-particles" in the present specification relates to particles having diameter ranged from about 5 to about 150 nm In some embodiments, in order for a particle to be considered a 'nano-particle,' a diameter of the particles must be at least 10 nm, or at least 20 nm, or at least 30 nm or at least 40 nm, or at least 50 nm, or at least 75 nm.

The term "micro-particles" in the present specification relates to particles having diameter ranged from about 151 nm to about 5 μm.

In some embodiments, the nano-particles may aggregate into an entity larger than a 'nano-particle.'

In some embodiments, the micro-particles may aggregate into entity larger than a 'micro-particle.'

When half-galvanic cell units are 'autonomous', the interior metal particles within the cell-unit are encapsulated by the inner and outer layer(s) so that the metal-particle so as to prevent chemical interaction between the encapsulated metal particles and the surrounding medium (e.g. cosmetically or pharmaceutically acceptable medium) in which the half-galvanic cell-units are suspended.

When half-galvanic cell units are 'individual' each unit is separately suspended within the medium—i.e. the half-galvanic cell units do not coalesce.

The non-polar surrounding medium, (liquid, semi-liquid, gel or paste-like), allows the formation of homogenous environment with the encapsulated half-galvanic cell units having external layer(s) of hydrophobic nano-particles.

Under such conditions, each of the individual encapsulated half-galvanic cell unit represents a separate, immiscible, autonomous hypertonic entity relative to the treated skin, wherein the optional plurality of individual hypotonic entities form the hypotonic component relative to the skin. As mentioned above, the individual half-galvanic cell units of different ox/red potentials (E°) form the battery effect described hereinafter.

In some embodiments, the composition simultaneously comprises (i) autonomous encapsulated half-galvanic cell units of hypertonic character, relative to the skin of treated baldness zone, as well as (ii) separated autonomous hypotonic entities. In exploring new methods for treating hair and vitalizing the activity of hair follicles, it was surprisingly and unexpectedly found that such composition that comprises distinct autonomous hypertonic and hypotonic entities are particularly useful and highly effective in topical application of regions with poorly active or totally inactive hair follicles. Such treatments are resulted in reviving or increasing hair follicles activity followed by renewal of hair growth from same follicles. More particularly, the presence, side by side, on the baldness zone surface of multiple encapsulated hypertonic entities (each represents a half-galvanic cell unit) and encapsulated hypotonic entities resulted in multidirectional flow of water from hypotonic environments to the hypertonic ones, inwardly, transversally and upwardly the treated baldness zone in the scalp. Thus, the presence of separate hypertonic and hypotonic entities forms a multidirectional flow of water inwardly, transversally and upwardly the treated baldness zone in the scalp. It is speculated that the multidirectional flow of water within the baldness zone plays an important role in removing from the follicle and vicinity accumulated materials having adverse effect on follicle normal functions. It seems that the flow of water into and within the baldness zone in the areas close to the follicles creates an external pressure on the follicular sheath, contributing to the sebum extraction. In addition, forming such multidirectional flow of water plays an important role in extending the time of functional battery effect that is created when the metal and ionic content of the half-galvanic cell units is slowly released following penetration of the baldness zone surface towards the hair follicle region.

Thus, in some embodiments, compositions of present invention are considered as capable of creating multiple complete galvanic cells within the skin of the treated baldness zone by incorporation of free half-galvanic cells of different ox/red potentials that are released from the encapsulated half-galvanic cell units.

According to an embodiment of present invention, the skin in the baldness zone is simultaneously treated with two compositions of different E°, such as:

(i) A composition which comprises encapsulated half-galvanic cell units, each contains Zn(s) and its soluble electrolytic salt (such as, for example, $ZnSO_4(aq)$, $ZnCl_2$ (aq) or $Zn(NO_3)_2$); and (ii) A composition which comprises encapsulated half-galvanic cell units, each contains Cu(s) and its soluble electrolytic salt (such as, for example, $CuSO_4(aq)$, $CuCl_2$ (aq) or $Cu(NO_3)_2$).

It is speculated that when such compositions of at least some embodiments are in contact with the skin in the baldness zone, they penetrate the skin along the hair shafts and release multiple half-galvanic cell units that are incorporated into multiple complete galvanic cells (referred herein to as "battery units") capable of generating electric current in the pico- to nano- amps range. These battery units function as battery cells, in the electrical conductivity environment of the baldness skin that also serves as an ionic bridge. It is further speculated that the formed battery units play a significant role in various electrical-dependent physiological processes, including activation of hair follicles.

As was mentioned before, the multidirectional flow of water plays an important role in extending the time of functional effect of the battery units that are created when the metals and ionic content of the half-galvanic cell units are released following penetration of the baldness skin pores and/or accumulation next to the hair shafts, in particular in the hair follicle regions.

It is further speculated that simultaneously pumping water into treated baldness area (by means of autonomous hypotonic entities), side by side with removing water from same area (by means of semi-galvanic hypertonic units) resulted in increasing the ions movement and the generation of electric current by multiple complete galvanic cells.

In some embodiments, when presently-disclosed compositions are applied for treating baldness zone with poorly active or inactive hair follicles, the individual encapsulated entities that are bounded by external layer(s) of hydrophobic nano-particles migrate to sites of hydrophobic character, such as, for example ducts of sebaceous glands and hair follicles. These externally hydrophobic encapsulated entities are attracted and adsorbed onto the surface of corresponding sites and are ruptured and/or opened along the line of contact zone which is formed between the surface of adsorbed encapsulated entities from the presently-disclosed compositions and the surface of the adsorbing sites. Thus, the location of ruptures and openings of each individual encapsulated entity is solely restricted to the surface area of said encapsulated entity that is in direct contact with surface of the corresponding adsorbing site (in the contact zone). Apart from the opening formed in the contact zone, the encapsulated entities remain intact and relatively stable for a while. Obviously, there is no water flow inside or outside the encapsulated entities through the intact encapsulating layers.

The adsorption of individual encapsulated entities onto corresponding sites within the baldness dermal layers, which is followed by rupture of the encapsulating layers along the contact zone, resulted in water flow from skin cells and/or intra-dermal spaces into the ruptured hypertonic entities, side by side with flow of water from ruptured hypotonic entities into skin cells and/or intra-dermal spaces. At the same time, the content of the half-galvanic cell units (which are of hypertonic character) is slowly released while creating an electric field of heterogeneous plurality of sites of multidirectional high potential gradients, within the baldness zone of the scalp. Further, as was mentioned above, the existence of released multiple half-galvanic cell units of different ox/red potentials within the baldness zone forms the "battery effect".

The "battery effect" provides a high gradient multidirectional electric field and generates an electric current in a pico- to nano-amps range, which leads to several beneficial effects:

It may affect the enzymatic activity which takes place in the follicle near the sebaceous gland. In particular, it may inhibit the activity of the enzyme 5α-reductase (by means of $Zn^{2+}(aq)$) and consequently, prevent the production of dihydrotestosterone (DHT) from testosterone.

It may stimulate biological activity of the scalp area side by side with regeneration of organelles' activity, in particular, regenerating follicular normal activity.

It may stimulate nerves ends, signaling the body for self-treatment.

As was pointed out the rupture of any individual encapsulated entity within the baldness skin is restricted, at least during the first and critical stage of the treatment, to the contact zone which is formed when surface of encapsulated entity is in contact with surface of the corresponding adsorbing site. Consequently, excluding the opening formed in the contact zone, such encapsulated entities retain their hypertonic and hypotonic entity discrete, separate, immiscible and stable, at least until the first and critical stage of the treatment.

Applying the compositions of present invention for treating baldness zone and for facilitating hair growth, comprises the step of coating the treated baldness skin surface with the compositions, optionally followed by patting or massaging the coated skin area for several minutes. This process increases the penetrability of the compositions particles towards their adsorbing sites in the skin Thus, for enhancing hair follicle's activity or revitalizing their activity, it is recommended to conduct daily successive treatments for at least two-to-six month period.

Some embodiments of present invention relate to the possibility of preparing a well controlled composition, as far as the number and size of a predefined particular type of encapsulated half-galvanic cell unit is concerned. For example, it is possible to prepare composition which comprises any desirable number of encapsulated half-galvanic cell units, optionally with any desirable number of encapsulated hypotonic entities.

The materials that are useful for encapsulating the half-galvanic cell units and for encapsulating the optional hypotonic entities are the following:
(i) hydrophilic metal (including silicon) oxide nano-particles which form the internal part of the encapsulating layers.
(ii) hydrophobic metal (including silicon) oxide nano-particles which form the external part of the encapsulating layers.

There is a wide range of hydrophilic metal (including silicon) oxide nanoparticles suitable for forming the internal part of the encapsulating layers. However, the preferred hydrophilic nanoparticles are selected from the group consisting of silica $SiO_2$, $Al_2O_3$, $TiO_2$, $Fe_2O_3$, MnO, ZnO, $CeO_2$ and combination thereof. Among these materials silica nanoparticles are mostly preferred.

Similarly, there is a wide range of hydrophobic metal (including silicon) oxide nanoparticles suitable for forming the external part of the encapsulating layers. However, in some embodiments, hydrophobic nanoparticles are preferably selected from the group consisting of silica $SiO_2$, $Al_2O_3$, $TiO_2$, $Fe_2O_3$, MnO, ZnO, $CeO_2$ and combination thereof which were modified to substantially display (at least 90%) hydrophobic character. This is done by substituting at least 90% of hydrophilic groups with equivalent number of non-polar hydrophobic groups. The mostly preferred hydrophobic nanoparticles are modified hydrophilic silica nanoparticles containing the group —Si(OR)n or —Si(R)n on their surface, wherein n represents 1, 2 or 3 and R represents a similar or different $C_1$-$C_6$ alkyl group. Hydrophobic silica nanoparticles in which R represents —$CH_3$ is the most preferable ones.

The metals and their salts that are useful for forming the encapsulated half-galvanic cell units are selectable according to differences in ox/red potentials (E°) and degree of toxicity. In other words, the selectable metals and their soluble electrolytic salts should be non-toxic to the skin or human body.

The non-polar medium in which the encapsulated entities are spread may be oil, such as, for example, jojoba oil, grape seed oil, lemon oil, wheat germ oil, calendula oil, chamomile oil, rosemarin oil, emu oil and cyclomethicone.

In addition, the non-polar medium may serve as a solvent for hydrophobic or lipophilic hair-treating ingredients. Examples of such ingredients are finasteride and minoxidil.

The composition of embodiments of may be in the form of, cream, paste, ointment, gel, aerosol and wet-powder (to distinguish from regular dry powder which does not comprise bounded or encapsulated water droplets).

EXAMPLES

Example 1

This Example relates to a composition (hereinafter referred to as "Composition Cu") comprising individual autonomous encapsulated half-galvanic cell units, wherein each half-galvanic cell unit comprises Cu(s) in the form of micro particles immersed in an aqueous solution of $CuCl_2$. The composition further comprises autonomous encapsulated water droplets as hypotonic entities, as well.

Composition Cu which displays positive E° ($Cu^{2+}$(aq)+ $2e^- \leftarrow\!\!\rightarrow$ Cu(s); E°=+0.34V) is capable of generating electric current when applies onto the skin in baldness zone in combination with other compositions of negative E°, such as Composition Zn (cf. example 2). More particularly, applying Composition Cu onto the scalp in combination with Composition Zn resulted in substantial improvement in preventing alopecia and/or renewing hair growth within a relatively short period—often several months.

Preparation of Composition Cu

A1. The Powder Containing Encapsulated Cu(s)+$CuCl_2$ (aq):

| N | Ingredients | % Wt |
|---|---|---|
| 1 | Purified water | 57 |
| 2 | Hydrophilic silica[1] | 1.7 |
| 3 | Hydrophobic silica[2] | 10.8 |
| 4 | Copper powder 3 micron[3] | 0.5 |
| 5 | Cooper chloride | 30 |
| 6 | Iodopropynyl butylcarbamate | 0.02 |

[1]Hydrophilic silica - Aerosil 380 (DeGussa)
[2]Hydrophobic Silica - Aerosil R812 (DeGussa)
[3]CI77400 (Copper powder, dendritic, 3 micron) by Sigma-Aldrich 57 g Purified distilled water are heated to 75° C. and 1.7 g Hydrophilic silica are added and mixed, following cooling the mixture to 35-40° C. 0.5 g Copper powder are added to the mixture and mixed in a mixer having a propeller rotating at about 600-800 rpm. 0.02 g Iodopropynyl butylcarbamate are added and mixed for about 5 min. 30 g Coper chloride are added to the formed mixture and mixed in a mixer having a propeller rotating at about 600-800 rpm for about 5-7 min. 10.8 g Hydrophobic silica are added to the mixture while mixing in the blender "Vita-Mix" having a propeller rotating at about 10000-12000 rpm for about 0.7-1 min to form a powder (referred herein to as "powder of Cu(s)+$CuCl_2$(aq)").

A2. Preparation of the Rest-hypotonic Powder for Composition Cu

| N | Ingredients | % Wt |
|---|---|---|
| 1 | Colloidal PMG-WP[4] | 37.8 |
| 2 | Pure water | 40.2 |
| 3 | Hydrophilic silica | 6 |
| 4 | Hydrophobic silica | 16 |
| 5 | Iodopropynyl butylcarbamate | 0.02 |

[4]Colloidal PMG-WP - Colloidal Gold (Grant Industries Inc.)

0.02 g Iodopropynyl butylcarbamate are mixed with 40.2 g of purified distilled water until they are completely dissolved. 37.8 of Colloidal PMG-WP are added to the mixture and mixed in a mixer having a propeller rotating at about 600-800 rpm (rotations per minute) for about 5 min. 6 g Hydrophilic silica are added To the formed mixture and mixed in a mixer having a propeller rotating at about 700-1000 rpm for about 5-10 min. In the last step, 16 g of hydrophobic silica are added and mixed in a mixer having a propeller rotating at about 2000-3500 rpm until a powder is formed (referred herein to as "Rest-hypotonic powder").

A3. Preparation of Composition Cu:

| N | Ingredients | % Wt |
|---|---|---|
| 1 | Rest-hypotonic powder | 19.3 |
| 2 | Powder of Cu(s) + $CuCl_2$(aq) | 19.3 |
| 3 | *Borago Officinalis* (Borage) Seed Oil | 30.1 |
| 4 | Jojoba oil | 10.3 |
| 5 | Nettle oil in Jojoba oil | 12 |
| 6 | Emu oil | 9 |
| 7 | Iodopropynyl butylcarbamate | 0.02 |

The following materials: 9.0 g Emu oil, 30.1 g *Borago Officinalis* (Borage) seed oil, 12.0 g Nettle in Jojoba oil, 10.3 Jojoba oil and 0.02 g Iodopropynyl butylcarbamate are inserted into a glass and mix in a mixer having a propeller rotating at about 600-800 rpm (rotations per minute) for about 5 min. The formed mixture is kept in a sterilized container (N1) to which 19.3 g Rest-hypotonic powder is added, followed by adding 19.3 g powder of Cu(s)+$CuCl_2$ (aq) while mixing the formed mixture until all powder is dispersed in the oil phase.

Other Compositions Cu may be prepared in which the soluble electrolytic salt is $Cu(NO_3)_2$ or $CuSO_4$. Further, the Cu(s) particles may be in the range of nano- to micro size and/or mixture thereof.

Example 2

This Example relates to a composition (hereinafter referred to as "Composition Zn") comprising individual autonomous encapsulated half-galvanic cell units, wherein each half-galvanic cell unit comprises Zn(s) particles in the range of nano- to micro size and/or mixture thereof immersed or suspended in an aqueous solution of $ZnSO_4$ ($ZnSO_4$(aq)).

The composition further comprises autonomous encapsulated water droplets as hypotonic entities, as well.

Composition Zn which displays negative E° ($Zn^{2+}$(aq)+ $2e^- \leftarrow\!\!\rightarrow$ Zn(s); E°=−0.76V) is capable of generating electric current when applies onto the skin in baldness zone in combination with other compositions of positive E°, such as Composition Cu (cf. example 1). More particularly, applying Composition Zn onto the scalp in combination with Composition Cu resulted in substantial improvement in preventing alopecia and/or renewing hair growth within a relatively short period—often several months.

Preparation of Composition Zn

A1. The Powder Containing Encapsulated Zn(s)+$ZnSO_4$:

| Ingredients | % Wt |
|---|---|
| 1 Purified water | 57 |
| 2 hydrophilic silica | 1.7 |
| 3 Hydrophobic silica | 10.8 |
| 4 Zinc powder | 0.5 |
| 5 Zinc sulfate | 30 |
| 6 Iodopropynyl butylcarbamate | 0.02 |

57 g Purified distilled water are heated to 75° C. and 1.7 g Hydrophilic silica are added and mixed, following cooling the mixture to 35-40° C. 0.5 g Zinc powder are added to the mixture and mixed in a mixer having a propeller rotating at about 600-800 rpm. 0.02 g Iodopropynyl butylcarbamate are added and mixed for about 5 min. 30 g Zinc sulfate are added to the formed mixture and mixed in a mixer having a propeller rotating at about 600-800 rpm for about 5-7 min.

10.8 g Hydrophobic silica are added to the mixture while mixing in the blender "Vita-Mix" having a propeller rotating at about 10000-12000 rpm for about 0.7-1 min to form a powder (referred herein to as "powder of Zn(s)+ ZnSO$_4$(aq)").

A2. Preparation of the Rest-hypotonic Powder for Composition Zn

For preparing the encapsulated hypotonic entities (Rest-hypotonic powder) see Example 1 above.

A3. Preparation of Composition Zn

| N | Ingredients | % Wt |
|---|---|---|
| 1 | Rest-hypotonic powder | 19.3 |
| 2 | Powder of Zn(s) + ZnSO$_4$(aq) | 19.3 |
| 3 | *Borago Officinalis* (Borage) Seed Oil | 30.1 |
| 4 | Jojoba oil | 10.3 |
| 5 | Nettle oil in Jojoba oil | 12 |
| 6 | Emu oil | 9 |
| 7 | Iodopropynyl butylcarbamate | 0.02 |

The following materials: 9.0 g Emu oil, 30.1 g *Borago Officinalis* (Borage) seed oil, 12.0 g Nettle in Jojoba oil, 10.3 Jojoba oil and 0.02 g Iodopropynyl butylcarbamate are inserted into a glass and mix in a mixer having a propeller rotating at about 600-800 rpm (rotations per minute) for about 5 min. The formed mixture is kept in a sterilized container (N2) to which 19.3 g Rest-hypotonic powder is added, followed by adding 19.3 g powder of Zn(s)+ZnSO$_4$ (aq) while mixing the formed mixture until all powder is dispersed in the oil phase.

Other Compositions Zn may be prepared in which the soluble electrolytic salt is Zn(NO$_3$)$_2$ or ZnCl$_2$. Further, the Zn(s) particles may be in the range of nano- to micro size and/or mixture thereof.

Example 3

This Example relates to Composition Cu which lacks autonomous encapsulated hypotonic water (or aqueous suspension) droplets.

Such composition is applicable for treating and/or preventing alopecia and for renewing hair growth. It may be applied alone or in combination with other compositions of present invention, such as, for example Composition Zn.

The Composition Cu (which lacks hypotonic entities) comprises the following ingredients:

| Ingredients | % Wt |
|---|---|
| Powder Cu(s) + CuCl$_2$ (aq)[1] | 32 |
| Cyclomethicone | 40 |
| Jojoba oil | 28 |
| Iodopropynyl butylcarbamate | 0.02 |

[1]Powder containing encapsulated Cu(s) + CuCl$_2$(aq) is prepared as described in Example 1.

Other Compositions Cu may be prepared in which the soluble electrolytic salt is Cu(NO$_3$)$_2$ or CuCl$_2$. Further, the Cu(s) particles may be in the range of nano- to micro size and/or mixture thereof.

Example 4

This Example relates to Composition Zn which lacks autonomous encapsulated hypotonic water (or aqueous suspension) droplets.

Such composition is applicable for treating skin and for preventing alopecia and/or renewing hair growth. It is applicable in combination with other compositions of present invention, such as, for example Composition Cu.

The Composition Zn (which lacks hypotonic entities) comprises the following ingredients:

| Ingredients | % |
|---|---|
| Powder Zn(s) + ZnSO$_4$(aq)[2] | 32 |
| Cyclomethicone | 40 |
| Jojoba oil | 28 |
| Iodopropynyl butylcarbamate | 0.02 |

[2]Powder containing encapsulated Zn(s) + ZnSO$_4$(aq) is prepared as described in Example 1

Other Compositions Zn may be prepared in which the soluble electrolytic salt is Zn(NO$_3$)$_2$ or ZnCl$_2$. Further, the Zn(s) particles may be in the range of nano- to micro size and/or mixture thereof.

Example 5

This Example relates to an independent, randomized, formal trial for evaluation the effectiveness of using the compositions of Examples 1 and 2 for renewing hair growth by baldness zones in heads of 18 male subjects 18 to 50 years old.

As far as procedure is concerned, each subject had 2 marked mini-baldness zones (randomized): one was not treated and used for control and the other was daily treated. Each daily treatment involved coating the marked baldness zone with a mixture of Composition Cu and Composition Zn.

This daily treatment was repeated 5 days a week.

Phototrichograms (macroscopic pictures of the scalp) were taken at t=0 and at t=6 weeks of each zone. Pictures were analyzed by experts.

After 6 weeks, the control zones showed <2% change in anagen hair counting.

The treated baldness zones showed an average increase of 10% in anagen hair counting. Reduction in numbers of hairs of telogen phase and increase in numbers of hairs of anagen phase was observed, as well. Thus, of the 18 treated subjects 14 have shown reduction of at least 3.5% in the numbers of telogen hairs, comparing to only 0.3% in the control zones.

General

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A composition comprising individual, autonomous encapsulated half-galvanic cell units having the same ox/red potential (E°), wherein each half-galvanic cell unit comprises metal particles in the range of nano- to micro size or a mixture thereof, suspended within an aqueous solution of soluble electrolytic salt of the same metal and wherein each half-galvanic cell unit is encapsulated by internal layer(s) and external layer(s), and wherein:
   a. the internal layer(s) are made of at least one of (i) hydrophilic metal oxide nanoparticles and (ii) hydrophilic silicon oxide nanoparticles; and
   b. the external layer(s) are made of at least one of (i) hydrophobic metal oxide nanoparticles and (ii) hydrophobic silicon oxide nanoparticles.

2. The composition of claim 1, wherein the encapsulated half-galvanic cell units are spread or suspended in a non-polar medium.

3. The composition of claim 2, wherein the non-polar medium is oil.

4. The composition claim 1, further comprises individual, autonomous encapsulated entities that are each hypotonic relative to human skin of the scalp, wherein each hypotonic entity is encapsulated by internal layer(s) and external layers, and wherein:
   a. the internal layer(s) are made of at least one of (i) hydrophilic metal oxide nanoparticles and hydrophilic silicon oxide nanoparticles and
   b. the external layer(s) made of at least one of (i) hydrophobic metal oxide nanoparticles and hydrophobic silicon oxide nanoparticles.

5. The composition according to claim 1, wherein the metal is Cu(s) and the soluble electrolytic salt is selected from the group consisting of $CuCl_2(aq)$, $Cu(NO_3)_2$ and $CuSO_4$.

6. The composition according to claim 1, wherein the metal is Zn(s) and the soluble electrolytic salt is selected from the group consisting of $ZnCl_2(aq)$, $Zn(NO_3)_2$ and $ZnSO_4$.

7. A composition according to claim 4, wherein the hypotonic entities are encapsulated water or aqueous solution droplets.

8. The composition according to claim 1, wherein the half-galvanic cell units are encapsulated by internal layer(s) of hydrophilic silica ($SiO_2$) nanoparticles and external layer(s) of hydrophobic silica nanoparticles of the general formula $—Si(OR)_n$ or $—Si(R)_n$, wherein n represents 1, 2 or 3 and R represents a $C_1$-$C_6$ alkyl.

9. The composition according to claim 4, wherein the hypotonic entities are encapsulated by internal layer(s) of hydrophilic silica nanoparticles and external layer(s) of hydrophobic silica nanoparticles of the general formula $—Si(OR)_n$ or $—Si(R)_n$, wherein n represents 1, 2 or 3 and R represents a $C_1$-$C_6$ alkyl.

10. A composition according to claim 1, wherein it is in a liquid, semi-liquid, gel or paste-like form.

11. A method comprising applying first and second compositions of to mammalian skin so that upon application or thereafter, the galvanic half-unit cells form galvanic cells in or on the mammalian skin, wherein each of the first and second composition comprises individual, autonomous encapsulated half-galvanic cell units having the same ox/red potential (E°), wherein each half-galvanic cell unit comprises metal particles in the range of nano- to micro size or a mixture thereof, suspended within an aqueous solution of soluble electrolytic salt of the same metal and wherein each half-galvanic cell unit is encapsulated by internal layers(s) and external layer(s), and wherein:
   a. the internal layer(s) are made of at least one of (i) hydrophilic metal oxide nanoparticles and (ii) hydrophilic silicon oxide nanoparticles; and
   b. the external layer(s) are made of at least one of (i) hydrophobic metal oxide nanoparticles and (ii) hydrophobic silicon oxide nanoparticles.

* * * * *